United States Patent [19]

Franks

[11] Patent Number: 4,874,793

[45] Date of Patent: Oct. 17, 1989

[54] USE OF PROTRIPTYLINE FOR THE TREATMENT OF MENTAL HEALTH PROBLEMS IN CHILDREN

[76] Inventor: Darrell Franks, 325 West Ormsby, Louisville, Ky. 40203

[21] Appl. No.: 226,133

[22] Filed: Jul. 29, 1988

[51] Int. Cl.⁴ .......................................... A61K 31/135
[52] U.S. Cl. ................................................ 514/656
[58] Field of Search ........................................ 514/656

[56] References Cited

U.S. PATENT DOCUMENTS

| | | | |
|---|---|---|---|
| 3,244,748 | 5/1966 | Tishler et al. | 260/562 |
| 3,271,451 | 9/1966 | Tishler et al. | 260/570 |
| 3,324,170 | 6/1967 | Kollonitsch | 260/471 |
| 3,372,196 | 5/1968 | Engelhardt | 260/570.8 |
| 3,445,519 | 5/1969 | Kollonitsch | 260/570.8 |
| 3,513,201 | 5/1970 | Tishler et al. | 260/570.8 |
| 3,922,305 | 11/1975 | Engelhardt | 260/570.8 |
| 4,136,116 | 1/1979 | Kyburz | 260/570.8 |

FOREIGN PATENT DOCUMENTS

| | | | |
|---|---|---|---|
| 281766 | 9/1967 | Australia | 9.63/9.64 |
| 742262 | 9/1966 | Canada | 260/571 |

OTHER PUBLICATIONS

Diagnostic and Statistical Manual of Mental Health Disorders pp. 43-44 (1980) American Psychiatric Association.
Physicians Desk Reference, Barnhart pp. 1349-1350 (1987)-(will be provided).
Dorfman, W. The use of Protriptyline (MK-20). As a Antidepressant; A Preliminary Report; Am. J. Psych. 126(594-595), (1963).
Vaisberg, M., Protriptyne in the Treatment of Depressive States, Dis. Nerv. Syst. 25 110-111, (1964).
Oltman & Friedman, Protriptyline in the Treatment of Depressive Reactions, Am. J. Psych. 122, 582-584, (1965).
Krakowski, Protriptyline in Treatment of Severe Depressions; A Long Range Pilot Study, Am. J. Psych. 121, (807-809), (1965).
Weinstock, R. et al., Effects of Protriptyline and Perphenazine in Neurotic Depressed Outpatients, J. Clin. Phar. 627-630, (1975).
Whyte, et al., Plasma Concentrations of Protriptyline and Clinical Effects in Depressed Women, Brit. J. Psych. 128, 384-390, (1976).
Kashani & Contwell, Etiology and Treatment of Childhood Depression: A Biopsychological Perspective; Child Psych. & Hum. Dev. 23(3), 348-351, (1984).
Coilbert, M. & Koepke, H. Oxazepam Protriptyline: A double-blind Phase II Evaluation of the Efficacy and Safety of the Combination Versus Placebain Neurotic, Depressed and Anxious Psychiatric Outpatients, Current Therapeutic Res. 18, No. 6, 825-838, (1975).
USP DI, 7th Ed. (1987), vol. 1, pp. 244-246, and 251-252.
MSD, Vivactil (Protriptyline HCL) package insert, issued Jul. 1986.

*Primary Examiner*—Stanley J. Friedman
*Assistant Examiner*—Richard M. Kearse
*Attorney, Agent, or Firm*—Scott R. Cox

[57] ABSTRACT

This invention discloses the use of a dibenzo cycloheptene deriative, generally known as protriptyline for the treatment of mental health problems in children, specifically Attention Deficit Syndrome or Attention Deficit Disorder. By administering the correct dosage of this drug, children have shown improved concentration, improved sleep patterns, less behavioral problems both in school and at home and an overall improvement in the child behavior. This new use for protriptyline is unexpected and is contraindicated in the literature since protriptyline has commonly been used only as a antidepressant for adults and not as a mild stimulant in the treatment of childhood mental health problems, such as Attention Deficit Disorder or Syndrome.

4 Claims, No Drawings

USE OF PROTRIPTYLINE FOR THE TREATMENT OF MENTAL HEALTH PROBLEMS IN CHILDREN

BACKGROUND OF INVENTION

1. Field of Invention

This invention relates to drugs for the treatment of mental health problems. More particularly, this invention relates to the use of a drug for the treatment of children who exhibit signs and symptoms of Attention Deficit Syndrome or Attention Deficit Disorder.

2. Prior Art

In this psychopharmacological era characterized by the search for new and more effective agents especially for the treatment of mental health disorders, it has become increasingly important to individually tailor the drug treatment program to achieve the maximum benefit for each patient.

Recently particular attention has been directed to the treatment of the mental health problems of children. One particular mental health condition in children that is receiving extensive investigation is Attention Deficit Syndrome (ADS) also known as Attention Deficit Disorder (ADD) in children. These conditions may or may not be associated with hyperactivity.

The problem is characterized by:
  a. Inattention. At least three of the following:
1. often fails to finish things he or she starts;
2. often doesn't seem to listen;
3. is easily distracted;
4. has difficulty concentrating on schoolwork or other tasks requiring sustained attention; and
5. has difficulty sticking to a play activity.
  b. Impulsivity: At least three of the following:
1. often acts before thinking;
2. shifts excessively from one activity to another;
3. has difficulty organizing work (this not being due to cognitive impairment);
4. needs a lot of supervision;
5. frequently calls out in class; and
6. has difficulty awaiting turn in games or group situations.
  c. Hyperactivity. At least two of the following:
1. runs about or climbs on things excessively;
2. has difficulty sitting still or fidgets excessively;
3. has difficulty staying seated;
4. moves about excessively during sleep; and
5. is always "on the go" or acts as if driven by a motor.
  d. Onset before the age of 7.
  e. Duration of at least six months
  f. Not due to schizophrenia, affective disorder, or severe or profound mental retardation.

Attention deficit disorder without hyperactivity:

The criteria for this disorder are the same as those for attention deficit disorder with hyperactivity except that the individual never has signs of hyperactivity. *Diagnostic and Statistical Manual of Mental Health Disorders*, Ed. 3, pp. 43–44 (1980); American Psychiatric Association.

Currently, the drugs of choice for ADD or ADS are methylphenidate, whose tradename by CIBA is Ritalin and pemoline whose tradename by Abbott is Cylert. Although Ritalin and Cylert have shown promise in the treatment of ADS and ADD in children, there are certain routine deficiencies in their use such as the highly addictive nature of both drugs, the short active life of both drugs, incomplete control of the symptoms, the "rebound" effect as the drugs wear off late in the day producing increased symptomatology, poor improvement in psycho-social and family involvement, and no improvement in sleep patterns. Further, even when Ritalin and Cylert are effective, alternative drugs should be available to allow the treating physician the option of choosing one drug over others depending on the needs of the individual patient.

During the early to mid 1960's much research was conducted in psychopharmacology in a class of chemicals which were useful in the treatment of depressive symptoms in adults. These compounds were tricylic compounds, more specifically referred to as dibenzocycloheptene derivative compounds. One of this class of antidepressant drugs is N-methyl-5H-dibenzo[a,d]cycloheptene-5-propylamine hydrochloride, medically known as "protriptyline" whose chemical formula is as follows:

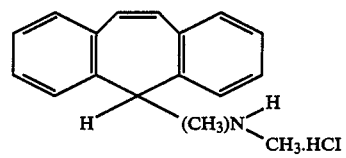

This product is produced commercially by Merck, Sharp and Dohme under the tradename Vivactil. In the *Physicians Desk Reference*, published by Edward R. Barnhart on pages 1349 through 1350, (1987), the use of Vivactil tablets is discussed. As stated in that reference, it is an antidepressant agent which is sometimes more effective than other tricylic antidepressant drugs such as imipramine or amitriptyline. It is considered particularly suitable for withdrawn and anergic patients. The drug has some minimal side effects of an anticholinergic nature particularly hypotensive and cardiovascular. However, the reference specifically states that "[t]he drug is not recommended for use with children because its safety and effectiveness in the pediatric age group has not been established."

N-methyl-5H-dibenzo[a,d]cycloheptene-5-propylamine hydrochloride was first disclosed in U.S. Pat. No. 3,244,748, Tishler et. al. where it was described as a drug for the treatment of mental health conditions "as it is an antidepressant and serves as a mood elevator or a psychic energizer." Column 3, lines 38 through 43.

Processes for the production of this product were disclosed in U.S. Pat. No. 3,271,451, Tishler et. al and U.S. Pat. No. 3,513,201, Tishler et. al. Other related chemical compounds also used in the treatment of mental health conditions are disclosed in Kollonitsch, U.S. Pat. No. 3,324,170; Engelhardt, U.S. Pat. No. 3,372,196; Kollonitsch; U.S. Pat. No. 3,445,519, Engelhardt, U.S. Pat. No. 3,922,305; and Kyburz et. al., U.S. Pat. No. 4,136,116. Related foreign patents include French Pat. No. 632,244, Swiss Pat. No. 415,611; Canadian Pat. No. 742,262, Tishler et. al.; and Australian Pat. No. 281766, Tishler et. al.

The use of protriptyline as a antidepressant has been discussed in several medical journal articles including Dorfman, W.; *The Use Of Protriptyline (MK-240) As A Antidepressant A Preliminary Report*, Am.J.Psych, 126, 594–595; (1963); Vaisberg, M., *Protriptyne in the Treatment of Depressive States*, Dis. Nerv. Syst. 25, 110–111 (1964); Oltman, J. and Friedman, S. *Protriptyline in the Treatment of Depressive Reactions*, Am.J. Psych. 122, 582–584 (1965); Krakowski, A. J., *Protriptyline in Treat-* ment Of Severe Depressions; A Long Range Pilot Study, Am.J. Psych. 121, 807–809, (1965); Weinstock, R. et. al., *Effects of Protriptyline and Perphenazine in Neurotic Depressed Outpatients,* J. Clin. Phar., 627–630, (1975), Whyte, S. F. et. al. *Plasma Concentrations of Protriptyline and Clinical Effects in Depressed Women,* Brit. J. Psych 128, 384–390, (1976) and Gilbert, M. and Koepke, H., *Oxazepam-Protriptyline: A Double-Blind Phase II Evaluation of the Efficacy and Safety of the Combination Versus Placebo in Neurotic, Depressed and Anxious Psychiatric Outpatients,* Current Therapeutic Research 18, No. 6, 825–838 (1975).

In addition to their use for the treatment of depression, tricylic compounds have been considered to be useful in the treatment of alcoholism, eating disorders, anxiety syndromes and some cases of obsessive compulsive disorders. For example, one of the current uses being investigated is the treatment of adult women with depression problems associated with premenstrual syndrome.

The tricylic compounds in general and protriptyline in particular have been used and are well accepted for the treatment of adult depression. However, the treatment of adults for depression has no relationship to the treatment of children for ADS or ADD since ADS or ADD are not considered to be affective disorders and diagnostic standards exclude childhood depressive disorders. (See previous discussion).

Adult depression is an entirely separate diagnostic category and does not include any of the diagnostic standards for attention deficit syndrome or disorder. Protriptyline is considered to be useful only in the treatment of adults with retarded depression characterized by hypersomulance, withdrawal from interpersonal activities and relationships, decreased energy levels, inertia, and lack of interest in most areas of life.

Adult depression is now considered to actively involve the serotonin pathway, and protriptyline is specific for the noradrenergic pathway. Thus, no common neurobiochemical pathway is known. Kashana, J. H. and Cantwell, D. P., *Etiology and Treatment of Childhood Depression: A Biopsychological Perspective.* Child Psych & Human Dev. 23(3), 348–351, (May, 1984).

These tricyclic compounds have not been used in the treatment of childhood mental health problems generally and ADS in particular. Occasionally imipramine, desipramine and amitriptyline have been used to treat childhood depression and enuresis with imipramine commonly being the drug of choice. No mention has been made of the use of protriptyline. Further, it is widely acknowledged that childhood depression as an illness varies significantly from ADS or ADD since ADS or ADD are not considered affective disorders.

Not only has the use of protriptyline been restricted, but the product information distributed by the manufacturer of the drug states that this drug is not recommended for the treatment of children. Although in the Vaisberg Article previously discussed, one 10 year old boy was treated with protriptyline, halting his enuresis, there have been no suggestion that the use of protriptyline would be effective for the treatment of ADS or ADD. In fact, protriptyline has not even been considered for the treatment of childhood depression.

Accordingly, it is an object of the present invention to use protriptyline for the treatment of childhood mental health problems.

It is a further object of this invention to use protriptyline in the treatment of Attention Deficit Syndrome (or Disorder) in children.

These and other objects, as well as the scope, nature, and utilization of the invention will be apparent to those skilled in the art from the following description and appended claims.

SUMMARY OF INVENTION

The present invention involves the use of N-methyl5H-dibenzo[a,d]cycloheptene-5propylamine hydrochloride in the treatment of childhood mental health problems, generally, and in particular for the treatment of attention deficit syndrome or disorder.

DETAILED DESCRIPTION OF INVENTION

As disclosed in U.S. Pat. Nos. 3,244,748, 3,271,451 and 3,513,201 which are incorporated by reference, certain cycloheptenes useful in the treatment of mental health conditions are prepared by the reaction of an alkali metal derivative of 5H-dibenzo[a,d]-cycloheptene with an N-(halopropyl)-N-methyl carbamic acid ester and the resulting urethane derivative is hydrolyzed to form the desired product. This process may be illustrated as follows:

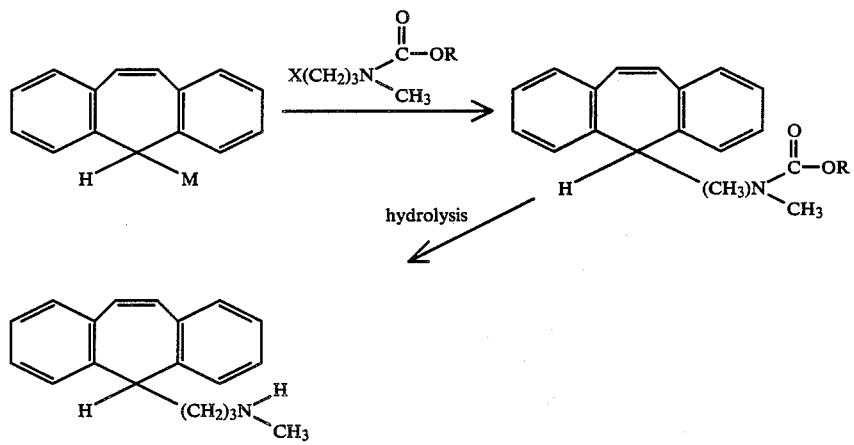

wherein M represents an alkali metal, X is a halogen and R is a radical selected from the group consisting of alkyl, cycloalkyl, aralkyl and aryl.

In a preferred embodiment the cycloheptene disclosed is N-methyl-5H-dibenzo[a,d]cycloheptene-5- propylamine hydrochloride as disclosed in following formula:

This compound is known in the industry as protriptyline.

The accepted use for protriptyline as discussed in the background to the invention is as a treatment for depression and similar mental health problems in adults. It has been surprisingly found that protriptyline when used in the proper dosage can be effective for the treatment of Attention Deficit Syndrome in children. It has been surprisingly found that by the use of the protriptyline, there have been decreased behavior problems, increased concentration, increased family involvement, and improved learning ability in children. This was a surprising result since protriptyline has never been utilized in children and thus, use is contraindicated from existing literature.

In application, the protriptyline as prepared by Merck, Sharp and Dohme and known as Vivactil, is used for the treatment of Attention Deficit Syndrome or Disorder and similar mental health problems in children under the age of 18 years. The maximum dosage is about 20.0 milligrams per child daily with children limited to about 1.0 milligram per kilogram of body weight. Although protriptyline has a mild stimulating effect which is somewhat similar to the effect of methylphenidate, commonly known as Ritalin, or pemoline, commonly known as Cylert, the direct patient benefit with the use of protriptyline over the other drugs is improved concentration, improved sleep patterns, less behavioral problems at home and in school and increased attentiveness. These improvements were dramatic and were in excess of those achieved by other drugs.

In the use for children, the protriptyline can be mixed with a liquid base comprised of liquid lactose and artificial coloring to produce a syrup-like compound which can be administered to children in a liquid form. This liquid base can be flavored with various fruit flavors, such as cherry, to make the administration of the drug easier. Further, the protriptyline can be blended with powdered lactose and artificial coloring and formed into chewable tablets which can be taken orally by children in an form easier than in the normal unflavored tablet form.

I claim:

1. A method of treating attention deficit syndrome or attention deficit disorder in children which comprises administering orally to said children a therapeutically effective amount of the chemical compound N-methyl-5H-dibenzo[a,d]cycloheptene-5-propylamine hydrochloride.

2. The method of claim 1 wherein said chemical compound is combined with a liquid lactose to produce a syrup-like compound for oral administration to children.

3. The method of claim 1 wherein said chemical compound is blended with powdered lactose to produce a chewable tablet for oral administration to children.

4. The method of claim 1 wherein the dosage of the chemical compound is limited to between about 1 milligram per kilogram of weight of the child up to a maximum of 20 milligrams per child per day.

* * * * *